United States Patent [19]
Polato

[11] Patent Number: 5,976,592
[45] Date of Patent: Nov. 2, 1999

[54] METHOD AND APPARATUS FOR STERILIZING BIOLOGICAL LIQUIDS, PARTICULARLY MILK AND ITS BY-PRODUCTS

[75] Inventor: Antonio Polato, Thiene, Italy

[73] Assignee: Officine Di Cartigliano S.P.A., Italy

[21] Appl. No.: 08/952,264

[22] PCT Filed: May 23, 1996

[86] PCT No.: PCT/EP96/02217

§ 371 Date: Feb. 23, 1998

§ 102(e) Date: Feb. 23, 1998

[87] PCT Pub. No.: WO96/37112

PCT Pub. Date: Nov. 28, 1996

[30] Foreign Application Priority Data

May 26, 1995 [IT] Italy .................................. V195A0088

[51] Int. Cl.$^6$ .............................. A23C 3/07; A01J 11/00
[52] U.S. Cl. ........................... 426/241; 426/522; 99/451; 99/452; 99/467; 422/21
[58] Field of Search ................................... 426/241, 522, 426/511, 524, 520, 521; 422/21; 219/701; 99/325, 331, 339, 451, 452, 453, 467

[56] References Cited

U.S. PATENT DOCUMENTS

| | | | |
|---|---|---|---|
| 5,403,564 | 4/1995 | Katschnig et al. | 422/307 |
| 5,697,291 | 12/1997 | Burgener et al. | 99/451 |

FOREIGN PATENT DOCUMENTS

| | | |
|---|---|---|
| 0 217 662 | 4/1987 | European Pat. Off. . |
| 0 497 099 | 8/1992 | European Pat. Off. . |
| 402211855 | 8/1990 | Japan . |
| 4126060 | 4/1992 | Japan . |
| 5067327 | 3/1993 | Japan . |
| 25823 | 12/1967 | Luxembourg . |
| 619495 | 3/1949 | United Kingdom . |
| 682064 | 11/1952 | United Kingdom . |
| 2 193 624 | 2/1988 | United Kingdom . |
| 2 274 568 | 7/1994 | United Kingdom . |
| WO95/00179 | 1/1995 | WIPO . |

OTHER PUBLICATIONS

"Deposit Formation in UHT Plants. I. Effect of Forewarming in Indirectly Heated Plants," *Milchwissenschaft*, by G.R. Patil et al., vol. 41 (6), 1986, pp. 337–339.

Primary Examiner—David Lacey
Assistant Examiner—Drew Becker
Attorney, Agent, or Firm—R. Neil Sudol; Henry D. Coleman

[57] ABSTRACT

Method and apparatus for the continuous sterilization of a non-packaged biological liquid, particularly milk and its byproducts, containing bacterial and sporal loads, including the steps of a) gradually preheating the liquid to a preheating temperature proximate to a maximum temperature of the process; b) irradiating the liquid with an electromagnetic field with a frequency of less than 1 GHz so as to heat the product to the maximum temperature of the process; and c) rapidly cooling the liquid to a temperature of approximately 15° before packaging. The preheating temperature attained during the preheating step a) is between 90° C. and 140° C. and the maximum temperature reached during the irradiation step b) is about 165° C. with a thermal gradient between about 0.1° C./s and 10° C./s, so as to provide a high temperature heating of the liquid while preventing destruction or alteration of the active principles and organoleptic properties of the liquid.

11 Claims, 2 Drawing Sheets

METHOD AND APPARATUS FOR STERILIZING BIOLOGICAL LIQUIDS, PARTICULARLY MILK AND ITS BY-PRODUCTS

The present invention relates to a method for sterilizing biological liquids, for alimentary, sanitary, and cosmetic use, in particular milk and its by-products.

Various methods for preserving and sterilizing milk are known. It is known that the main components of this food product are constituted by water, sugars, mineral salts, fats, vitamins, biochemical compounds, such as enzymes, antibodies, and hormones, together with biological components of microbial and viral origin. Namely, milk is an emulsified solution of lactose, casein, fats, and some mineral salts in a water content of more than 85%. The pathogenic microorganisms that are present in this food product constitute the so-called bacterial flora, which includes, among others, Mycrobacterium tuberculosis, a wide range of viruses, including the poliomyelitis virus, as well as thermoresistant, thermophilic, psycrophilic and anaerobic germs.

The problem that must be solved by the sterilization of these products essentially consists in the total destruction of the bacterial flora without affecting the active principles that determine the original organoleptic, chemical and physical properties of the products allowing a shelf life comprised between 4 and 9 months depending on the national legislation.

Conventional preservation methods used on an industrial scale are of the physical, chemical-physical, chemical, and biological types. In particular, physical methods use refrigeration, heat transmission, or desiccation.

Among these methods, processes based on the application of heat are by far the most effective and most widespread in solving the above mentioned problems. The heat application conditions depend not only on the nature of the product to be treated but also on the type of microorganisms contained in it and finally on the simultaneous use or not of other preservation processes. The degree of heat resistance of the microorganisms has to be linked to external and environmental factors, such as the initial microbial concentration of the medium, the characteristics of the medium itself, and the time and temperature parameters, as well as to intrinsic factors such as the heat resistance of germs and spores.

In the conventional sterilization method, the product is superheating to temperatures of over 140° C. for a time between 5 and 12 minutes.

The temperature and duration of the thermal treatment depend on the heat application method and on the type of product. Furthermore, at the end of the treatment the product must be subjected to cooling down to temperatures of less than 35° C. before introducing it in sterilized containers (glass bottles or Tetra-pak® containers).

Heat can be applied by indirect exchange, in which the product and the heating medium are separated by the wall of an exchanger, or by direct exchange, in which the product and the heating medium are in direct contact.

Current thermal preservation methods are the most important ones from the industrial point of view, but have some drawbacks.

In fact, in order to increase the sterilization effectiveness, it is necessary to increase the maximum temperature of the process, with the consequence of damaging the product from the organoleptic, physical and chemical point of view, destroying proteins and essential enzymes and giving it a cooked or burnt taste or reducing its natural taste and aroma.

Furthermore, in indirect-transmission systems the heat is transmitted from the outside inward, so that it is necessary to increase the temperature of the exchange surface in order to destroy the microorganisms even in the innermost regions. This can cause a partial non-uniformity and ineffectiveness of the process.

In direct-exchange systems, the heating medium is generally constituted by steam, which has the inconvenience of condensing inside the product itself, thereby reducing the concentration of the active principles; the steam must be eliminated before the condensation (degassing).

Electronic preservation devices without an exchange surface have recently been devised which are based on the following principle.

Microorganisms, like all living organisms, are notoriously poor conductors of electricity and heat. Because of this, application of heat to these organisms is difficult and slow and furthermore occurs unevenly. In practice, due to their low electrical conductivity, microorganisms behave like dielectric particles that become aligned within an external electric field.

By using the above described physical principle, electronic preservation methods entail immersing the product in a high-frequency alternating electric or electromagnetic field for a period that is sufficient to cause the structural degeneration of the pathogenic microorganisms.

The Japanese patent application published as No. 2-211855, filed on Feb. 10, 1989, describes a method and an apparatus for sterilizing a liquid food product by irradiation with high-frequency electromagnetic waves.

In this known method, the radiation is constituted by microwaves at frequencies above 1 GHz, which are emitted by a magnetron oscillator and are transmitted axially inside a waveguide, with very short irradiation times on the order of a few seconds. Due to the high frequency and short wavelength of the electromagnetic waves, shielding is necessary to protect the assigned personnel that works in the surrounding environment. Moreover, the intense superheating caused by the microwaves forces to perform very short treatments in quick succession, each treatment being followed by intense cooling to keep the product below the temperature at which its organoleptic chemical and physical properties change.

Patents U.S. Pat. No. 2,576,862, U.S. Pat. No. 3,272,636, FR-A-2 547 732, and DE-A-2 628 234 describe other methods and apparatuses that use electromagnetic waves whose frequencies are in the microwave and/or radiofrequency range. These known methods and apparatuses are applied to already-packaged products and always require appropriate shielding against emissions that are harmful to the human body.

Furthermore, since the destructive action of the alternating electromagnetic field affects not only the pathogenic microorganisms but also the active principles that determine the organoleptic properties of the products to be preserved, these known methods and apparatuses cause a reduction of these organoleptic properties, reducing the value of the active principles.

There are also known methods and apparatuses for preserving edible liquids with electromagnetic waves, in the radiofrequency field, with or without a conventional preheating. However, the results of such methods are still unsatisfactory according to both the microbacteria and enzymatic tests.

EP-A-0 497 099 discloses a method and an apparatus for the preserving biological products comprising all the features mentioned in the preamble of the independent claims 1 and 8, wherein the maximum temperature of the process is approximately 50° C. Even if such temperature affords excellent protection of the active principles and organoleptic properties of the treated products as well as considerable saving of energy, according to the national legislations it does not guarantee the complete destruction of the microorganisms and a a safe sterilization of the treated products.

GB-A-619 495 relates to a short-time high-temperature method and apparatus for treating milk and other liquids wherein the products are preheated with conventional means to a temperature of about 140° F. (60° C.) and finally heated through a high frequency electromagnetic field to a temperature of about 205° F. (96° C.) lower that the boiling temperature of the products. Also in this case, the relatively low maximum temperature of the process does not ensure the complete sterilization of the products. Moreover, since the increment of temperature is effected in less than one second, the thermal gradient is higher than 36° C./s and therefore the products are subject to a very strong thermal shock.

The article of "Milchwissenshaft" vol 41, No 6, 1986, pages 337–339 discusses the effects of forewarming on formation of deposits in conventional UHT plants which normally operate to a maximum temperature of 140° C. with no direct heating though electromagnetic waves of high frequency.

The aim of the present invention is to obviate the above drawbacks, providing a method for the continuous sterilization of non-packaged liquid food and non-food products that allows complete and uniform preservation in high-reliability conditions, leaving the organic and organoleptic properties of the treated products unchanged.

The method and the apparatus according to the invention provide for a particularly effective sterilization because of the radiofrequency irradiation in one or more passages only during the high temperature treatment and for a very short time, preventing the destruction or alteration of the active principles and of the organic and organoleptic properties of the products.

Further characteristics and advantages will become apparent from the detailed description of a method and a device according to the invention, illustrated only by way of non-limitative example in the accompanying drawings, wherein.

Figure 1:
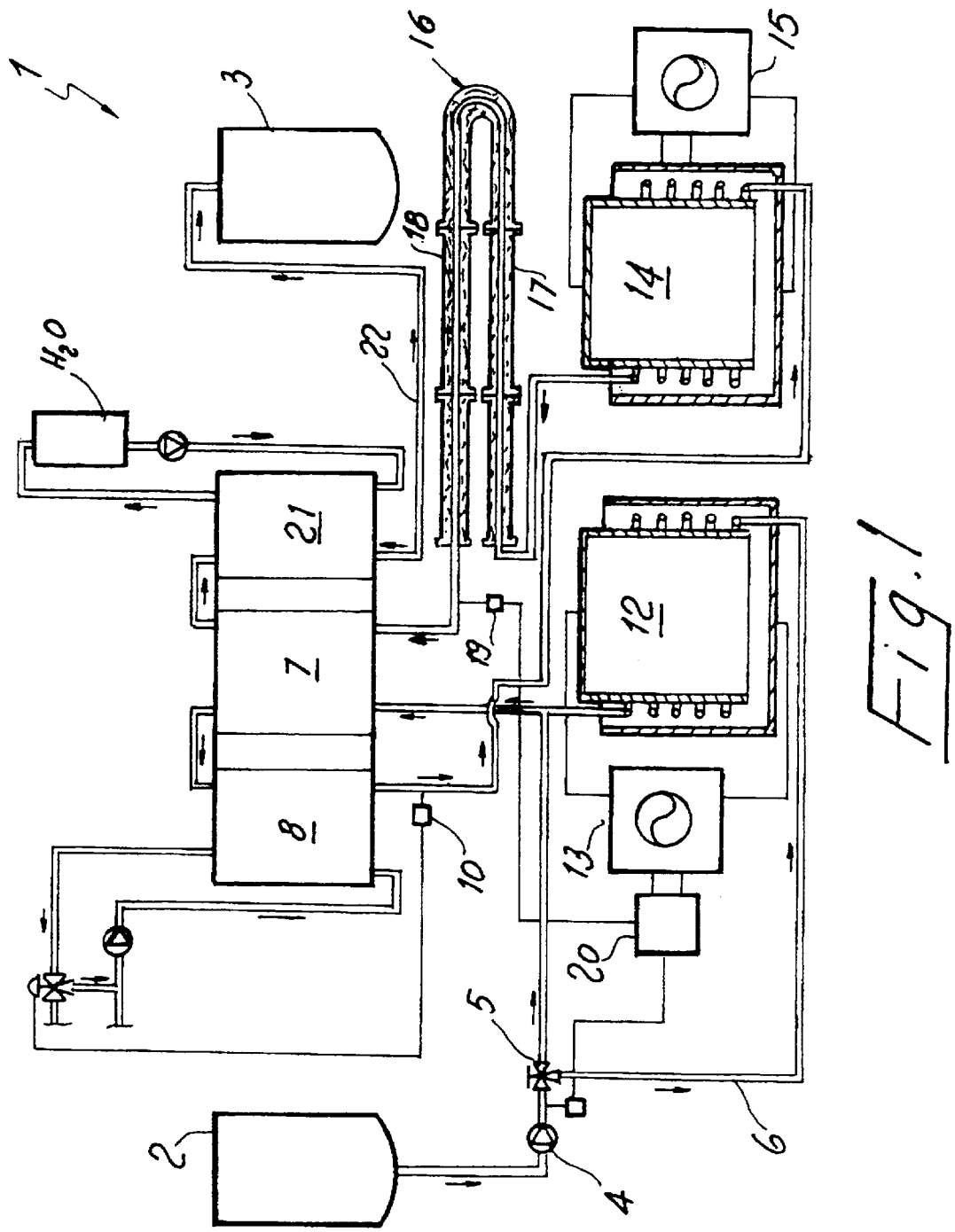
FIG. 1 is a schematic view of a preferred embodiment of a sterilization apparatus according to the invention.

With reference to FIG. 1, this figure shows an apparatus for continuous sterilization according to the invention, generally designated by the reference numeral 1.

This apparatus includes a reservoir 2, made for example of stainless steel, for storing the product to be treated; the reservoir is connected to a vessel 3 that is similar to the preceding one, for collecting the treated product by virtue of a hydraulic circuit. A variable-delivery pump 4 is arranged in series to the reservoir 2, with a shunt valve 5 which conveys the product contained in the reservoir 2 through the pipe 6 of the circuit toward the primary circuit of a preheater 7, for example of the plate countercurrent type, which uses the superheated product itself as heating fluid.

Downstream of the preheater 7 there is a superheater 8 that uses a heating fluid—for example pressurized water at a temperature of approximately 150° C., that is contained in an external circuit 9 that is provided with a controlled bypass valve 10, or, alternatively, saturated steam directly injected in the product to be treated. At the output of the superheater 8 there is a temperature sensor 11 that controls the valve 10 so as to keep the temperature of the product between 90° C. and 140° C., and preferably at about 130° C.

Downstream of the superheater 8 there is a first irradiation section, generally designated by the reference numeral 12, of the open type, for example having cylindrical symmetry, of the type described in Italian patent no. 1247067, so as to perform extremely uniform RF (radio-frequency) heating, for example up to a maximum temperature of approximately 165° C., for a relatively short time between for example 3 and 20 seconds, preferably for about 13 seconds.

Figure 2:
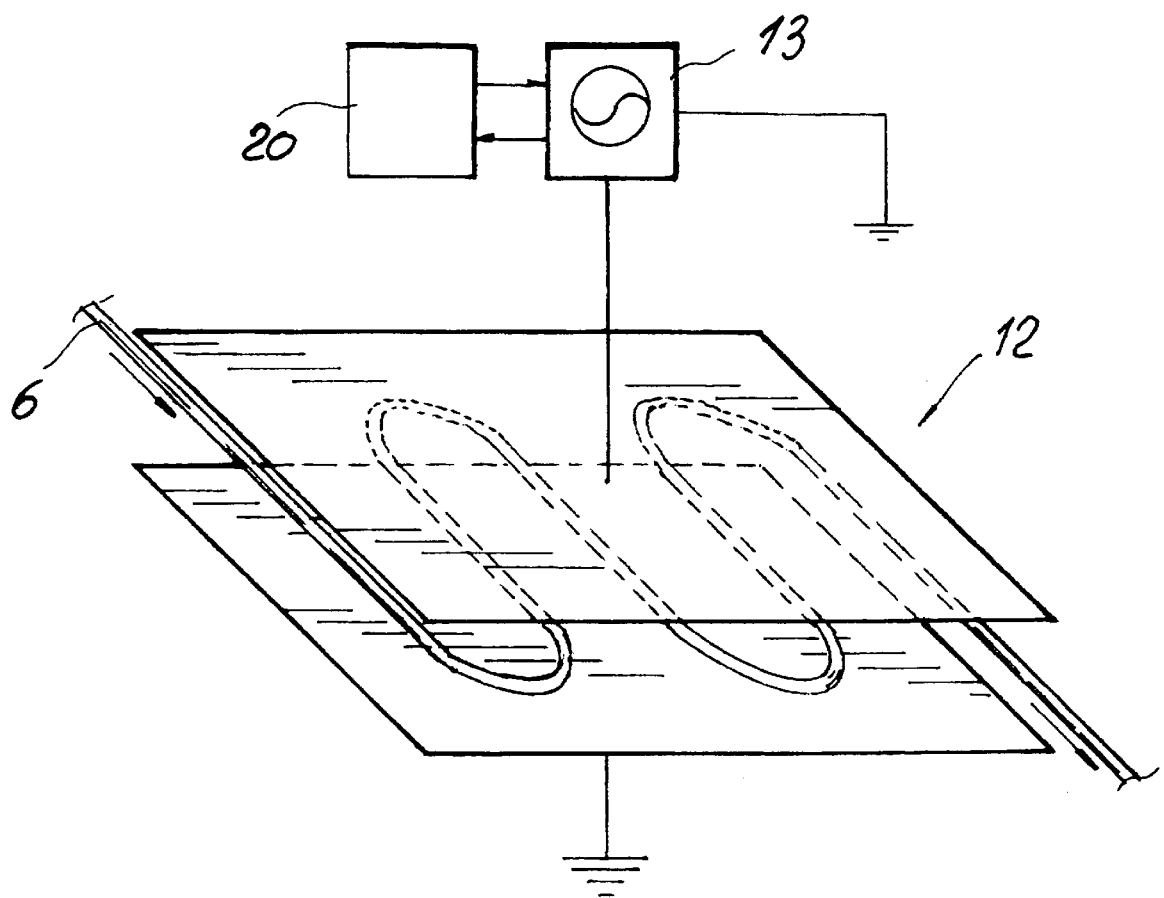
FIG. 2 is a view of a detail of the apparatus of FIG. 1, according to a second preferred embodiment of the invention.

Alternatively, the irradiation section may have a planar symmetry, of the type described in the cited Italian patent, and constituted by a pair of planar and parallel sheets and by a tubing interposed therein and made of a dielectric material in the shape of a coil wherein the product flows, as schematically illustrated in FIG. 2.

The cylindrical and coaxial plates of the irradiation section 12 are connected to a triode oscillator 13 or the like, set to generate radio waves at a frequency between 6 and 915 MHz, for example of about 27 MHz. The power of the electromagnetic field is selected in a range between 0.01 KW/l (10 KW/m$^3$) and 30 KW/l (3000 KW/m$^3$) according to the composition of the product and to its bacterial concentration, measured beforehand by sampling bacterial swabs.

Because of the relatively high value of the wavelength of the radio waves emitted by the irradiation section, the apparatus does not require specific shielding for environmental safety, with the consequence of limiting the complexity and cost of the apparatus and of allowing its use in conventional installations without risks for the assigned personnel.

The product that leaves the irradiation section 12 is conveyed to the secondary circuit of the preheater 7, or of a steam generator, not illustrated in the drawings, so as to recover part of the irradiation heat.

Then the product that leaves the preheater 7 is sent to a second irradiation section 14 that is similar to the preceding one but is connected to a second triode generator 15 or the like that is suitable to generate radio waves at a substantially different frequency with respect to the first generator, for example a frequency that is about twice as high, so as to perform the RF sterilization of the residual spores.

The product that leaves the second irradiation section is degassed by eliminating the steam possibly injected during the pre-heating and then sent to an irradiated product holding region, with outgoing branches 17 and return branches 18 at a substantially constant temperature to allow completion of the process for destroying the bacterial loads.

At the output of the portion 18 of the holding region 16 there is a temperature sensor 19 that sends an electrical signal to a control unit 20 for controlling the oscillator 13 so as to keep the final temperature of the irradiated product below 165° C. An auxiliary cooling unit, not shown in the drawings, may furthermore be optionally provided between each turn of the dielectric duct of the irradiation section, to ensure that the maximum preset temperature is never exceeded.

At the output of the holding section 16, the fluid is fed into the secondary circuit of the preheater 7, which it leaves at approximately 30–35° C., and then is fed into the main circuit of a refrigeration unit 21 that uses a mixture of water and glycol, kept at approximately 0° C. by an appropriate chiller, as coolant. The product, cooled to a final temperature of approximately 15° C., is fed through the pipe portion 22 toward the collecting container 3, from which it is removed to be packaged in adapted containers or aseptic packages.

I claim:

1. A method for the continuous sterilization of a non-packaged biological liquid, containing bacterial and sporal loads, comprising the steps of:
   a) gradually preheating the liquid to a preheating temperature;
   b) irradiating the liquid with an electromagnetic field with a frequency of less than 1 GHz so as to heat the liquid to a maximum temperature of the process; and
   c) rapidly cooling the liquid to a temperature of approximately 15° C. before packaging;
   said preheating temperature attained during said preheating step a) being between 90° C. and 140° C. and said maximum temperature reached during said irradiation step b) being about 165° C. with a thermal gradient between about 0.1° C./s and 10° C./s so as to provide a high temperature heating of the liquid while preventing destruction or alteration of the active principles and organoleptic properties of the liquid.

2. Method according to claim 1 wherein the irradiation time of said irradiation step b) is between approximately 3 and approximately 20 seconds.

3. Method according to claim 1 wherein said preheating step a) is accomplished by injection of saturated steam.

4. Method according to claim 1 wherein the irradiation step b) is followed by an intermediate cooling step in which the liquid is cooled to a temperature that is equal to said preheating temperature, followed by a second irradiation step with radio frequency (RF) radiation whose frequency is different from the frequency of the electromagnetic energy used in said irradiating step b).

5. Method according to claim 4 wherein said RF radiation has a frequency about twice as high as the frequency of the electromagnetic energy used in said irradiating step b).

6. Method according to claim 5 wherein the frequency of said RF radiation used in said second irradiation step and the frequency of the electromagnetic energy used in said irradiating step b) are both between about 6 MHz and 915 MHz.

7. Method according to claim 6 wherein the frequency of said RF radiation used in said second irradiation step and the frequency of the electromagnetic energy used in said irradiating step b) are both between about 13 MHz and 96 MHz.

8. Method according to claim 1, wherein the electromagnetic field has a specific energy in a range between 0.01 kW/l (10 kW/m$^3$) and 30 kW/l (3000 kW/m$^3$).

9. Apparatus for the continuous sterilization of a non-packaged biological product, containing bacterial and sporal loads, comprising:
   a conduit for connecting a tank for the product to be treated to a container for collecting the product after treatment thereof;
   a preheating section in said conduit for preheating the product to a preheating temperature;
   a first irradiation section in said conduit having means for irradiating the product with an oscillating high-frequency electromagnetic field operating in a range below 1 GHZ for heating the product to a maximum temperature;
   a confinement apparatus for confining the product within said electromagnetic field;
   a second irradiation section in said conduit operating at a frequency different from a frequency of operation of said first irradiation section, for irradiating the product downstream in said conduit with respect to said first irradiation section;
   a control unit for adjusting the power and frequency of the electromagnetic field and the irradiation time of said first irradiation section as a function of the composition and concentration of the bacterial and sporal loads of the product;
   a temperature maintenance unit located downstream in said conduit with respect to said first irradiation section; and
   a cooling section in said conduit for cooling the product to a temperature of approximately 15° C.;
   said control unit being constructed so as to drive said preheating section to preheat the product to said preheating temperature between approximately 90° C. and 140° C. and for adjusting the energy of said electromagnetic field to heat the product to said maximum temperature proximate to 165° C. with a thermal gradient between about 0.1° C./s and 10° C./s so as to provide a high temperature heating of the product while preventing destruction or alteration of the active principles and organoleptic properties of the product.

10. Apparatus according to claim 9 wherein the frequency of operation of said second irradiation section is about double the frequency of operation of said first irradiation section.

11. Apparatus according to claim 9 wherein said preheating section comprises a saturated steam injector.

* * * * *